US00RE38200E

(19) United States

(12) Reissued Patent

Watjen et al.

(10) Patent Number: US RE38,200 E

(45) Date of Reissued Patent: Jul. 22, 2003

(54) INDOLE-2,3-DIONE-3-OXIME DERIVATIVES

(75) Inventors: Frank Watjen, Ballerup (DK); Jorgen Drejer, Ballerup (DK)

(73) Assignee: NeuroSearch A/S, Glostrup (DK)

(21) Appl. No.: 09/956,892

(22) PCT Filed: Oct. 1, 1997

(86) PCT No.: PCT/DK97/00418

§ 371 (c)(1),
(2), (4) Date: Jun. 1, 1998

(87) PCT Pub. No.: WO98/14447

PCT Pub. Date: Apr. 9, 1998

Related U.S. Patent Documents

Reissue of:

(64) Patent No.: 6,124,285
Issued: Sep. 26, 2000
Appl. No.: 09/077,554
Filed: Jun. 1, 1998

(30) Foreign Application Priority Data

Oct. 1, 1996 (DK) ..... 1069/96
Nov. 13, 1996 (DK) ..... 1277/96

(51) Int. Cl.[7] ..... A61K 31/5375; A61K 31/4375; C07D 471/04; C07D 417/12

(52) U.S. Cl. ..... 514/232.8; 514/292; 544/126; 546/82

(58) Field of Search ..... 546/81; 514/292, 514/232.8; 544/126

(56) References Cited

U.S. PATENT DOCUMENTS 5,721,230 A 2/1998 Harris et al.
5,801,174 A * 9/1998 Moldt et al. ..... 514/217
5,917,053 A * 6/1999 Moldt et al. ..... 548/433

FOREIGN PATENT DOCUMENTS

EP 529636 A1 * 3/1993
EP 633262 A1 * 1/1995
HU 215954 11/1995
WO WO 9426747 A1 * 11/1994
WO WO 9608494 A1 * 3/1996
WO WO 9608495 A1 * 3/1996

OTHER PUBLICATIONS

JPET, Nielsen et al., vol. 289(3), pp. 1492–1501, 1999.*

* cited by examiner

*Primary Examiner*—Evelyn Mei Huang
(74) *Attorney, Agent, or Firm*—Birch, Stewart, Kolasch & Birch, LLP

(57) ABSTRACT

The present invention relates to novel indole-2,3-dione-3-oxime derivatives capable of antagonising the effect of excitatory amino acids, such as glutamate. More specifically the novel indole-2,3-dione-3-oxime derivatives of the invention may be described by general formula (I), wherein $R^3$ represents "Het", or a group of formula (II), wherein "Het" represents a saturated or unsaturated, 4 to 7 membered, monocyclic, heterocyclic ring, at least one of $R^{31}$, $R^{32}$, and $R^{33}$ independendy represents hydrogen, alkyl, or hydroxyalkyl, and at least one of $R^{31}$, $R^{32}$, and $R^{33}$ independently represents $(CH_2)_nR^{34}$; wherein $R^{34}$ represents hydroxy, carboxy, alkoxycarbonyl, alkenyloxycarbonyl, alkynyloxycarbonyl, cycloalkoxycarbonyl, cycloalkylalkoxycarbonyl, aryloxycarbonyl, aralkoxycarbonyl, $CONR^{35}R^{36}$, or "Het"; wherein n is 0, 1, 2, or 3; and $R^5$ represents phenyl, naphthyl, thienyl, or pyridyl, all of which may be substituted. "A" represents a ring of five to seven atoms fused with the benzo ring at the positions marked "a" and "b", and formed by the following bivalent radicals: a-$NR^6$—$CH_2$—$CH_2$-b; a-$CH_2$—$NR^6$—$CH_2$-b; a-$CH_2$—$CH_2$—$NR^6$-b; a-$NR^6$—$CH_2$—$CH_2$—$H_2$-b; a-$CH_2$—$NR^6$—$CH_2$—$CH_2$-b; a—$CH_2$—$CH_2$—$NR^6$—$CH_2$-b; a-$CH_2$—$CH_2$—$CH_2$—$NR^6$-b; a-$NR^6$—$CH_2$—$CH_2$—$CH_2$—$CH_2$-b; a-$CH_2$—$NR^6$—$CH_2$—$CH_2$—$CH_2$-b; a-$CH_2$—$CH_2$—$NR^6$—$CH_2$—$CH_2$-b; a-$CH_2$—$CH_2$—$CH_2$—$NR^6$—$CH_2$-b; or a-$CH_2$—$CH_2$—$CH_2$—$CH_2$—$NR^6$-b; wherein $R^6$ represents hydrogen alkyl or $CH_2CH_2OH$; or a pharmaceutically acceptable salt thereof.

6 Claims, No Drawings

INDOLE-2,3-DIONE-3-OXIME DERIVATIVES

Matter enclosed in heavy brackets [ ] appears in the original patent but forms no part of this reissue specification; matter printed in italics indicates the additions made by reissue.

This application is the national phase under 35 U.S.C. §371 of prior PCT International Application No., PCT/DK97/00418, which has an International filing date of Oct. 1, 1997, which designated the United States of America, the entire contents of which are hereby incorporated by reference.

TECHNICAL FIELD

The present invention relates to novel indole-2,3-dione-3-oxime derivatives capable of antagonising the effect of excitatory amino acids, such as glutamate. The invention also relates to a method of preparing the chemical compounds of the invention, to pharmaceutical compositions comprising the chemical compounds, and a method of treatment herewith.

BACKGROUND ART

Excessive excitation by neurotransmitters can cause the degeneration and death of neurones. It is believed that this degeneration is in part mediated by the excitotoxic actions of the excitatory amino acids (EAA), glutamate and aspartate, at the N-methyl-D-aspartate (NMDA), the alfa-amino-3-hydroxy-5-methyl-4-isoxazole propionic acid (AMPA) receptor, and the kainate receptor. This excitotoxic action is responsible for the loss of neurones in cerebrovascular disorders such as cerebral ischemia or cerebral infarction resulting from a range of conditions, such as thromboembolic or haemorrhagic stroke, cerebral vasospasm, hypoglycaemia, cardiac arrest, status epilepticus, perinatal asphyxia, anoxia such as from near-drowning, pulmonary surgery and cerebral trauma as well as lathyrism, Alzheimer's, and Huntington's diseases. Compounds capable of blocking excitatory amino acid receptors are therefore considered useful for the treatment of the above disorders and diseases, as well as Amyotrophic Lateral Sclerosis (ALS), schizophrenia, Parkinsonism, epilepsy, anxiety, pain and drug addiction.

SUMMARY OF THE INVENTION

It is an object of the present invention to provide novel indole-2,3-dione-3-oxime derivatives which are excitatory amino acid antagonists and useful in the treatment of disorders or diseases of mammals, including humans, which are responsive to excitatory amino acid receptor antagonists.

Accordingly, in its first aspect, the invention provides the novel indole-2,3-dione-3-oxime derivatives described in claim 1.

In another aspect the invention relates to the use of a chemical compound of the invention for the preparation of a pharmaceutical composition.

In a third aspect the invention provides a pharmaceutical composition comprising a therapeutically effective amount of the chemical compound of the invention together and a pharmaceutically acceptable excipient, carrier or diluent.

In a fourth aspect the invention relates to the use of a chemical compound of the invention for the manufacture of a pharmaceutical composition for the treatment of a disorder or disease of a mammal, including a human, which disorder or disease is responsive to glutamic and/or aspartic acid receptor antagonists.

In a more specific aspect the invention relates to the use of a chemical compound of the invention for the manufacture of a pharmaceutical composition for the treatment a cerebrovascular disorder, lathyrism, Alzheimer's disease, Huntington's diseases, amyotrophic lateral sclerosis (ALS), schizophrenia, Parkinsonism, epilepsy, anxiety, pain or drug addiction.

In a fifth aspect the invention provides a method of treating disorders or diseases of living animals, including humans, which are responsive to excitatory amino acid receptor antagonists, comprising administering to a living animal body, including a human, in need thereof an effective amount of a chemical compound of the invention.

In a more specific aspect the invention provides a method of treating a cerebrovascular disorder, lathyrism, Alzheimer's disease, Huntington's diseases, amyotrophic lateral sclerosis (ALS), schizophrenia, Parkinsonism, epilepsy, anxiety, pain or drug addiction.

In a sixth aspect the invention relates to the use of the chemical compound of the invention in a method of treating a disorder or disease of a mammal, including a human, which disorder or disease is responsive to glutamic and/or aspartic acid receptor antagonists, said method comprising administering to a living animal body, including a human, in need thereof an effective amount of the chemical compound.

In a more specific aspect the invention relates to the use of the chemical compound of the invention in a method of treating a cerebrovascular disorder, lathyrism, Alzheimer's disease, Huntington's diseases, amyotrophic lateral sclerosis (ALS), schizophrenia, Parkinsonism, epilepsy, anxiety, pain or drug addiction.

In a seventh aspect the invention provides a method of preparing a chemical compound of the invention.

Other objectives of the present invention will be apparent to the skilled person hereinafter.

DETAILED DISCLOSURE OF THE INVENTION

Indole-2,3-dione-3-oxime Derivatives

In its first aspect, the present invention provides novel indole-2,3-dione-3-oxime derivatives. The novel indole-2,3-dione-3-oxime derivatives may be described by the general formula (I):

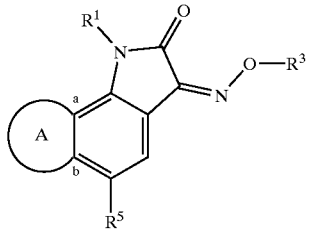

wherein $R^1$ represents hydrogen, alkyl or benzyl;

$R^3$ represents "Het", or a group of the following formula

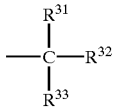

wherein

"Het" represents a saturated or unsaturated, 4 to 7 membered, monocyclic, heterocyclic ring, which ring may optionally be substituted one or more times with substituents selected from the group consisting of halogen, alkyl, alkoxy, and oxo; and at least one of $R^{31}$, $R^{32}$, and $R^{33}$ independently represents hydrogen, alkyl, or hydroxyalkyl, and at least one of $R^{31}$, $R^{32}$, and $R^{33}$ independently represents $(CH_2)_nR^{34}$;

wherein $R^{34}$ represents hydroxy, carboxy, alkoxycarbonyl, alkenyloxycarbonyl, alkynyloxycarbonyl, cycloalkoxycarbonyl, cycloalkyl-alkoxycarbonyl, aryloxycarbonyl, aralkoxycarbonyl, $CONR^{35}R^{36}$ or "Het";

wherein $R^{35}$ and $R^{36}$ represents hydrogen, alkyl, alkenyl, alkynyl, hydroxyalkyl, cycloalky, aryl, aralkyl, or $(CH_2)_n$—$R^{37}$;

wherein $R^{37}$ represents hydroxy, carboxy, alkoxycarbonyl, alkenyloxycarbonyl, alkynyloxycarbonyl, cycloalkoxycarbonyl, cycloalkyl-alkoxycarbonyl, aryloxycarbonyl, or aralkoxycarbonyl; or $R^{35}$ and $R^{36}$ together with the N-atom to which they are attached form a saturated 5- to 6-membered, heterocyclic ring, optionally containing one additional N or O atom; and "Het" is as defined above; and n is 0, 1, 2, or 3; and $R^5$ represents phenyl, naphthyl, thienyl, or pyridyl, all of which may be substituted one or more times with substituents selected from the group consisting of halogen, $CF_3$, $NO_2$, amino, alkyl, alkoxy, phenyl and $SO_2NR^{51}R^{52}$, wherein $R^{51}$ and $R^{52}$ each independently represents hydrogen or alkyl; or $R^{51}$ and $R^{52}$ together with the N-atom to which they are attached form a saturated 4- to 7-membered, monocyclic, heterocyclic ring, optionally containing one additional N or O atom; and "A" represents a ring of five to seven atoms fused with the benzo ring at the positions marked "a" and "b", and formed by the following bivalent radicals:

a-$NR^6$—$CH_2$—$CH_2$-b;

a-$CH_2$—$NR^6$—$CH_2$-b;

a-$CH_2$—$CH_2$—$NR^6$-b;

a-$NR^6$—$CH_2$—$CH_2$—$CH_2$-b;

a-$CH_2$—$NR^6$—$CH_2$—$CH_2$-b;

a-$CH_2$—$CH_2$—$NR^6$—$CH_2$-b;

a-$CH_2$—$CH_2$—$CH_2$—$NR^6$-b;

a-$NR^6$—$CH_2$—$CH_2$—$CH_2$—$CH_2$-b;

a-$CH_2$—$NR^6$—$CH_2$—$CH_2$—$CH_2$-b;

a-$CH_2$—$CH_2$—$NR^6$—$CH_2$—$CH_2$-b;

a-$CH_2$—$CH_2$—$CH_2$—$NR^6$—$CH_2$-b; or a-$CH_2$—$CH_2$—$CH_2$—$CH_2$—$NR^6$-b; wherein $R^6$ represents hydrogen, alkyl or $CH_2CH_2OH$; or a pharmaceutically acceptable salt thereof.

In a more preferred embodiment, the novel indole-2,3-dione-3-oxime derivatives may be described by the general formula (I), above, wherein "Het" is a lactone ring of the general formula (VI):

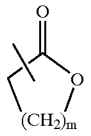

and wherein m is 1,2,3 or 4; and

In another preferred embodiment, the novel indole-2,3-dione-3-oxime derivatives may be described by the general formula (II):

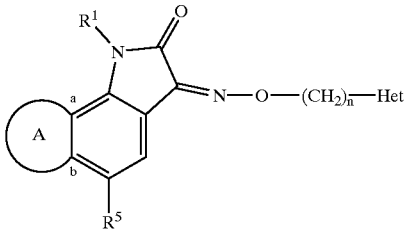

wherein $R^1$ represents hydrogen, alkyl or benzyl;

"Het" represents a saturated or unsaturated, 4 to 7 membered, monocyclic, heterocyclic ring, which ring may optionally be substituted one or more times with substituents selected from the group consisting of halogen, alkyl, alkoxy, and oxo;

n is 0, 1, 2, or 3;

$R^5$ represents phenyl, naphthyl, thienyl, or pyridyl, all of which may be substituted one or more times with substituents selected from the group consisting of halogen, $CF_3$, $NO_2$, amino, alkyl, alkoxy, phenyl and $SO_2NR^{51}R^{52}$; wherein $R^{51}$ and $R^{52}$ each independently represents hydrogen or alkyl; or $R^{51}$ and $R^{52}$ together with the N-atom to which they are attached form a saturated 4- to 7-membered, monocyclic, heterocyclic ring, optionally containing one additional N or O atom; and "A" represents a ring of five to seven atoms fused with the benzo ring at the positions marked "a" and "b", and formed by the following bivalent radicals:

a-$NR^6$—$CH_2$—$CH_2$-b;

a-$CH_2$—$NR^6$—$CH_2$-b;

a-$CH_2$—$CH_2$—$NR^6$-b;

a-$NR^6$—$CH_2$—$CH_2$—$CH_2$-b;

a-$CH_2$—$NR^6$—$CH_2$—$CH_2$-b;

a-$CH_2$—$CH_2$—$NR^6$—$CH_2$-b;

a-$CH_2$—$CH_2$—$CH_2$—$NR^6$-b;

a-$NR^6$—$CH_2$—$CH_2$—$CH_2$—$CH_2$-b;

a-$CH_2$—$NR^6$—$CH_2$—$CH_2$—$CH_2$-b;

a-$CH_2$—$CH_2$—$NR^6$—$CH_2$—$CH_2$-b;

a-$CH_2$—$CH_2$—$CH_2$—$NR^6$—$CH_2$-b; or a-$CH_2$—$CH_2$—$CH_2$—$CH_2$—$NR^6$-b; wherein $R^6$ represents hydrogen, alkyl or $CH_2CH_2OH$.

In a more preferred embodiment, the novel indole-2,3-dione-3-oxime derivatives may be described by the general formula (II), above, wherein n is 0, 1 or2; and $R^5$ represents phenyl or pyridyl, both of which may be substituted one or more times with substituents selected from the group consisting of halogen, $CF_3$, $NO_2$, amino, alkyl, alkoxy, phenyl and $SO_2NR^{51}R^{52}$; wherein $R^{51}$ and $R^{52}$ each independently represents hydrogen or alkyl; or $R^{51}$ and $R^{52}$ together with the N-atom to which they are attached form a chain —$(CH_2)_m$—, wherein m is 2, 3, 4, 5 or 6.

In another preferred embodiment, the novel indole-2,3-dione-3-oxime derivatives may be described by the general formula (III):

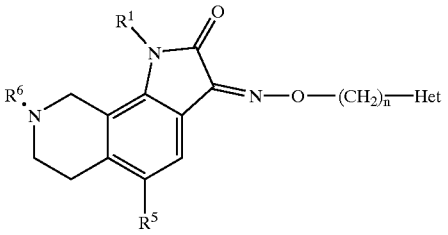

wherein $R^1$, $R^5$, $R^6$, "Het", and n are as defined above.

In a yet more embodiment, the novel indole-2,3-dione-3-oxime derivatives may be described by the general formula (II), wherein "Het" is a lactone of the general formula (VII):

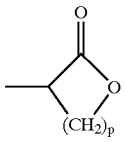

wherein p is 1, 2, 3, or 4.

In another preferred embodiment, the novel indole-2,3-dione-3-oxime derivatives may be described by the general formula (IV):

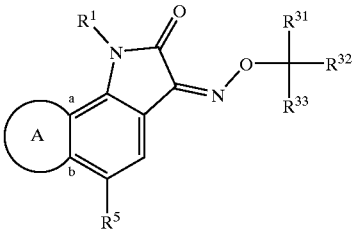

wherein $R^1$ represents hydrogen, alkyl or benzyl;

at least one of $R^{31}$, $R^{32}$, and $R^{33}$ independently represents hydrogen, alkyl, or hydroxyalkyl, and at least one of $R^{31}$, $R^{32}$, and $R^{33}$ independently represents $(CH_2)_nR^{34}$; wherein $R^{34}$ represents hydroxy, carboxy, alkoxycarbonyl, alkenyloxycarbonyl, alkynyloxycarbonyl, cycloalkoxycarbonyl, cycloalkyl-alkoxycarbonyl, aryloxycarbonyl, aralkoxycarbonyl, or $CONR^{35}R^{36}$; wherein $R^{35}$ and $R^{36}$ represents hydrogen, alkyl, alkenyl, alkynyl, hydroxyalkyl, cycloalkyl, aryl, aralkyl, or $(CH_2)_n$—$R^{37}$; wherein $R^{37}$ represents hydroxy, carboxy, alkoxycarbonyl, alkenyloxycarbonyl, alkynyloxycarbonyl, cycloalkoxycarbonyl, cycloalkyl-alkoxycarbonyl, aryloxycarbonyl, or aralkoxycarbonyl; or $R^{35}$ and $R^{36}$ together with the N-atom to which they are attached form a saturated 5- to 6-membered, heterocyclic ring, optionally containing one additional N or O atom; and n is 0, 1, 2, or 3; or one of $R^{31}$, $R^{32}$, and $R^{33}$ represents hydrogen or alkyl, and two of $R^{31}$, $R^{32}$, and $R^{33}$ together form a lactone ring of the general formula (VI):

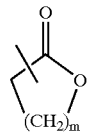

wherein m is 1, 2 or 3; and $R^5$ represents phenyl, naphthyl, thienyl, or pyridyl, all of which may be substituted one or more times with substituents selected from the group consisting of halogen, $CF_3$, $NO_2$, amino, alkyl, alkoxy, phenyl and $SO_2NR^{51}R^{52}$; wherein $R^{51}$ and $R^{52}$ each independently represents hydrogen or alkyl; or $R^{51}$ and $R^{52}$ together with the N-atom to which they are attached form a saturated 4- to 7-membered, monocyclic, heterocyclic ring, optionally containing one additional N or O atom; and "A" represents a ring of five to seven atoms fused with the benzo ring at the positions marked "a" and "b", and formed by the following bivalent radicals:

a-$NR^6$—$CH_2$—$CH_2$-b;
a-$CH_2$—$NR^6$—$CH_2$-b;
a-$CH_2$—$CH_2$—$NR^6$-b;
a-$NR^6$—$CH_2$—$CH_2$—$CH_2$-b;
a-$CH_2$—$NR^6$—$CH_2$—$CH_2$-b;
a-$CH_2$—$CH_2$—$NR^6$—$CH_2$-b;
a-$CH_2$—$CH_2$—$CH_2$—$NR^6$-b;
a-$NR^6$—$CH_2$—$CH_2$—$CH_2$—$CH_2$-b;
a-$CH_2$—$NR^6$—$CH_2$—$CH_2$—$CH_2$-b;
a-$CH_2$—$CH_2$—$NR^6$—$CH_2$—$CH_2$-b;
a-$CH_2$—$CH_2$—$CH_2$—$NR^6$—$CH_2$-b; or
a-$CH_2$—$CH_2$—$CH_2$—$CH_2$—$NR^6$-b; wherein R represents hydrogen, alkyl or $CH_2CH_2OH$;

or a pharmaceutically acceptable salt thereof.

In a more preferred embodiment, the novel indole-2,3-dione-3-oxime derivatives may be described by the general formula (V):

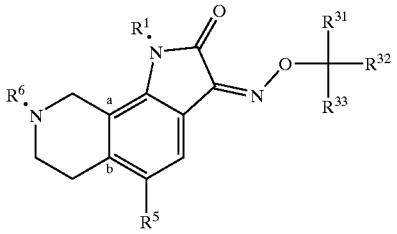

wherein $R^1$, $R^{31}$, $R^{32}$, $R^{33}$, $R^5$, and $R^6$ are as defined under formula (IV) above.

Definition of Substituents

In the context of this invention alkyl designates a straight chain or a branched chain containing of from one to six carbon atoms ($C_1$–$C_6$ alkyl), including but not limited to methyl, ethyl, propyl, isopropyl, butyl, isobutyl, t-butyl, pentyl and hexyl. In a preferred embodiment of this invention alkyl represents a $C_1$–$C_4$ alkyl, preferably a $C_1$–$C_3$ alkyl, most preferred methyl, ethyl, propyl or isopropyl.

In the context of this invention cycloalkyl designates a cyclic alkyl containing of from three to seven carbon atoms ($C_3$–$C_7$ cycloalkyl), including but not limited to cyclopropyl, cyclobutyl, cyclopentyl, and cyclohexyl.

In the context of this invention alkenyl designates a group containing of from two to six carbon atoms ($C_2$–$C_6$ alkenyl), including at least one double bond, for example, but not limited to ethenyl, 1,2- or 2,3-propenyl, 1,2-, 2,3-, or 3,4-butenyl.

In the context of this invention alkynyl designates a group containing of from two to six carbon atoms ($C_2$–$C_6$alkynyl), including at least one triple bond, for example, but not limited to ethynyl, 1,2- or 2,3-propynyl, 1,2-, 2,3- or 3,4-butynyl.

In the context of this invention cycloalkyl-alkyl designates a cycloalkyl as defined above which is attached to an alkyl as also defined above, e.g. cyclopropylmethyl.

In the context of this invention aryl designates an aromatic hydrocarbon, such as phenyl or naphthyl.

In the context of this invention aralkyl designates an aryl as defined above which is attached to an alkyl as also defined above, e.g. benzyl.

In the context of this invention alkoxy designates an alkyl-O— where alkyl is as defined above.

In the context of this invention alkoxycarbonyl designates an alkyl-O-CO— where alkyl is as defined above.

In the context of this invention cycloalkoxycarbonyl designates a cycloalkyl-O-CO— where cycloalkyl is as defined above.

In the context of this invention cycloalkyl-alkoxycarbonyl designates a cycloalkyl-alkyl-O-CO— where cycloalkylalkyl is as defined above.

In the context of this invention alkenyloxycarbonyl designates an alkenyl-O-CO— where alkenyl is as defined above.

In the context of this invention alkynyloxycarbonyl designates an alkynyl-O-CO— where alkenyl is as defined above.

In the context of this invention aryloxycarbonyl designates an aryl-O-CO— where aryl is as defined above.

In the context of this invention aralkoxycarbonyl designates an aralkyl-O-CO— where aralkyl is as defined above.

In the context of this invention halogen represents fluorine, chlorine, bromine and iodine.

In the context of this invention amino represents $NH_2$, NH-alkyl, or N-(alkyl)$_2$, wherein alkyl is as defined above.

In a more specific aspect, the novel indole-2,3-dione-3-oxime derivatives of the invention is 8-methyl-5-(4-(N,N-dimethylsulfamoyl)phenyl)-6-7-8-9-tetrahydro-1H-pyrrolo[3,2-h]-isoquinoline-2,3-dione-3-O-(3-(2-oxo)tetrahydrofuryl)oxime;

8-methyl-5-(4-(N,N-dimethylsulfamoyl)phenyl)-6-7-8-9-tetrahydro-1H-pyrrolo[3,2h]-isoquinoline-2,3-dione-3-O-(5-(4-bromo-3-methoxy)isoxazolylmethyl)oxime;

8-methyl-5-(4-(N,N-dimethylsulfamoyl)phenyl)-6-7-8-9-tetrahydro-1H-pyrrolo[3,2h]-isoquinoline-2,3-dione-3-O-(5-(4-bromo-3-ethoxy)isoxazolylmethyl)oxime;

8-methyl-5-(4-(N,N-dimethylsulfamoyl)phenyl)-6-7-8-9-tetrahydro-1H-pyrrolo[3,2h]-isoquinoline-2,3-dione-3-O-(4-(N,5-dimethyl-3-oxo)-isoxazolylmethyl)oxime;

8-methyl-5-(4-(N,N-dimethylsulfamoyl)phenyl)-6-7-8-9-tetrahydro-1H-pyrrolo[3,2h]-isoquinoline-2,3-dione-3-O-(4-(N-methyl-5-tertbutyl-3-oxo)isoxazolylmethyl)oxime;

8-methyl-5-(4-(N,N-dimethylsulfamoyl)phenyl)-6-7-8-9-tetrahydro-1H-pyrrolo[3,2h]- isoquinoline-2,3-dione-3-O-(4-(5-methyl-3-methoxy)isoxazolylmethyl)oxime; or 8-methyl-5-(4-(N,N-dimethylsulfamoyl)phenyl)-6-7-8-9-tetrahydro-1H-pyrrolo[3,2h]-isoquinoline-2,3-dione-3-O-(4-(5-methyl-3-ethoxy)isoxazolylmethyl)oxime;

or a pharmaceutically acceptable salt hereof.

In another specific embodiment, the novel indole-2,3-dione-3-oxime derivatives of the invention is 1-methyl-8-methyl-5-phenyl-6,7,8,9-tetrahydro-pyrrolo[3,2-h]-isoquinoline-2,3-dione-3-O-(carboxymethyl)oxime;

1-methyl-8-methyl-5-phenyl-6,7,8,9-tetrahydro-1H-pyrrolo[3,2h]-isoquinoline-2,3-dione-3-O-(ethoxycarbonylmethyl)oxime;

1-methyl-8-methyl-5-(4-(N,N-dimethylsulfamoyl)phenyl)-6,7,8,9-tetrahydropyrrolo[3,2-h]isoquinoline-2,3-dione-3-O-(carboxymethyl)oxime;

1-methyl-8-methyl-5-(4-(N,N-dimethylsulfamoyl)phenyl)-6,7,8,9-tetrahydro-1H-pyrrolo[3,2-h]isoquinoline-2,3-dione-3-O-(1-ethoxycarbonyl-1-methylethyl)oxime;

1-methyl-8-methyl-5-(4-(N,N-dimethylsulfamoyl)phenyl-6,7,8,9-tetrahydropyrrolo[3,2-h]isoquinoline-2,3-dione-3-O-(ethoxycarbonylmethyl)oxime;

8-methyl-5-phenyl-6,7,8,9-tetrahydro-1H-pyrrolo[3,2-h]isoquinoline-2,3-dione-3-O-(1-carboxy-1-methylethyl)oxime;

8-methyl-5-phenyl-6,7,8,9-tetrahydro-1H-pyrrolo[3,2-h]isoquinoline-2,3-dione-3-O-(1-carboxy-1-methylethyl)oxime;

8-methyl-5-phenyl-6,7,8,9-tetrahydro-1H-pyrrolo[3,2-h]isoquinoline-2,3-dione-3-O-(ethoxycarbonylmethyl)oxime;

8-methyl-5-phenyl-6,7,8,9-tetrahydro-1H-pyrrolo[3,2-h]isoquinoline-2,3-dione-3-O-(isopropoxycarbonylmethyl)oxime;

8-methyl-5-phenyl-6,7,8,9-tetrahydro-1H-pyrrolo[3,2-h]isoquinoline-2,3-dione-3-O-(1-ethoxycarbonyl-1-methyl)ethyloxime;

8-methyl-5-phenyl-6,7,8,9-tetrahydro-1H-pyrrolo[3,2-h]isoquinoline-2,3-dione-3-O-(t-butoxycarbonylmethyl)oxime;

8-methyl-5-phenyl-6,7,8,9-tetrahydro-1H-pyrrolo[3,2-h]isoquinoline-2,3-dione-3-O-(N,N-dimethylcarbamoylmethyl)oxime;

8-methyl-5-phenyl-6,7,8,9-tetrahydro-1H-pyrrolo[3,2-h]isoquinoline-2,3-dione-3-O-(N-methylcarbamoylmethyl)oxime;

8-methyl-5-phenyl-6,7,8,9-tetrahydro-1H-pyrrolo[3,2-h]isoquinoline-2,3-dione-3-O-(N-phenylcarbamoylmethyl)oxime;

8-methyl-5-phenyl-6,7,8,9-tetrahydro-1H-pyrrolo[3,2-h]isoquinoline-2,3-dione-3-O-(N,N-di(2-hydroxyethyl)carbamoylmethyl)oxime;

8-methyl-5-phenyl-6,7,8,9-tetrahydro-1H-pyrrolo[3,2-h]isoquinoline-2,3-dione-3-O-(morpholinocarbonylmethyl)oxime;

8-methyl-5-phenyl-6,7,8,9-tetrahydro-1H-pyrrolo[3,2-h]isoquinoline-2,3-dione-3-O-(ethoxycarbonylmethylcarbamoylmethyl)oxime;

8-methyl-5-phenyl-6,7,8,9-tetrahydro-1H-pyrrolo[3,2-h]isoquinoline-2,3-dione-3-O-(N,N-di(2-(N,N-diethylamino)ethyl)carbamoyl)oxime;

8-methyl-5-(4-(N,N-dimethylsulfamoyl)phenyl)-6,7,8,9-tetrahydro-1H-pyrrolo[3,2-h]-isoquinoline-2,3-dione-3-O-(carboxymethyl)oxime;

8-methyl-5-(4-(N,N-dimethylsulfamoyl)phenyl)-6,7,8,9-tetrahydro-1H-pyrrolo[3,2-h]isoquinoline-2,3-dione-3-O-(2-hydroxyethyl)oxime;

8-methyl-5-(4-(N,N-dimethylsulfamoyl)phenyl)-6,7,8,9-tetrahydro-1H-pyrrolo[3,2-h]isoquinoline-2,3-dione-3-O-(1-carboxy- 1-methylethyl)oxime;

8-methyl-5-(4-(N,N-dimethylsulfamoyl)phenyl-6,7,8,9-tetrahydro-1H-pyrrolo[3,2-h]isoquinoline-2,3-dione-3-O-(ethoxycarbonylmethyl)oxime;

8-methyl-5-(4-(N,N-dimethylsulfamoyl)phenyl-6,7,8,9-tetrahydro-1H-pyrrolo[3,2-h]isoquinoline-2,3-dione-3-O-(cyclopropylmethoxycarbonylmethyl)oxime;

8-methyl-5-(4-(N,N-dimethylsulfamoyl)phenyl-6,7,8,9-tetrahydro-1H-pyrrolo[3,2-h]isoquinoline-2,3-dione-3-O-(isopropoxycarbonylmethyl)oxime;

8-methyl-5-(4-(N,N-dimethylsulfamoyl)phenyl-6,7,8,9-tetrahydro-1H-pyrrolo[3,2-h]isoquinoline-2,3-dione-3-O-(N,N-dimethyl-carbamoylmethyl)oxime;

8-methyl-5-(4-(N,N-dimethylsulfamoyl)phenyl-6,7,8,9-tetrahydro-1H-pyrrolo[3,2-h]isoquinoline-2,3-dione-3-O-(piperidinocarbonylmethyl)oxime;

8-methyl-5-(4-(piperdinosulfonyl)phenyl-6,7,8,9-tetrahydro-1H-pyrrolo[3,2-h]isoquinoline-2,3-dione-3-O-(piperidinocarbonylmethyl)oxime;

8-methyl-5-(4-(N,N-dimethylsulfamoyl)phenyl-6,7,8,9-tetrahydro-1H-pyrrolo[3,2-h]isoquinoline-2,3-dione-3-O-(morpholinocarbonylmethyl)oxime; or 8-methyl-5-(4-(N,N-dimethylsulfamoyl)phenyl)6-7-8-9-tetrahydro-1H-pyrrolo[3,2-h]isoquinoline-2,3-dione-3-O-(4-hydroxybutyric acid-2-yl)oxime;

or a pharmaceutically acceptable salt hereof.

Steric Isomers

Some of the chemical compounds of the present invention exist in (+) and (−) forms as well as in racemic forms.

Racemic forms can be resolved into the optical antipodes by known methods, for example, by separation of diastereomeric salts thereof, with an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or I- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "Enantiomers, Racemates, and Resolution", John Wiley and Sons, New York (1981).

Moreover, being oximes, the chemical compounds of the invention may exist in two forms, syn- and anti-form, depending on the arrangement of the substituents around the —C═N— double bond. A chemical compound of the present invention may thus be the syn- or the anti-form, or it may be a mixture hereof.

Pharmaceutically Acceptable Salts

The novel indole-2,3-dione-3-oxime derivatives of the invention may be provided in any form suitable for the intended administration. Suitable forms include pharmaceutically (i.e. physiologically) acceptable salts.

Examples of pharmaceutically acceptable addition salts include inorganic and organic acid addition salts such as the hydrochloride, hydrobromide, phosphate, nitrate, perchlorate, sulphate, citrate, lactate, tartrate, maleate, fumarate, mandelate, benzoate, ascorbate, cinnamate, benzenesulfonate, methanesulfonate, stearate, succinate, glutamate, glycollate, toluene-p-sulphonate, formate, malonate, naphthalene-2-sulphonate, salicylate and the acetate. Such salts are formed by procedures well known in the art.

Other acids such as oxalic acid, while not in themselves pharmaceutically acceptable, may be useful in the preparation of salts useful as intermediates in obtaining a chemical compound of the invention and its pharmaceutically acceptable acid addition salt.

Metal salts of a chemical compound of the invention includes alkali metal salts, such as the sodium salt, of a chemical compound of the invention containing a carboxy group.

The chemical compound of the invention may be provided in solved or dissolved form together with a pharmaceutically acceptable solvents such as water, ethanol and the like. In general, solved forms are considered equivalent to dissolved forms for the purposes of this invention.

Pharmaceutical Compositions

In another aspect the invention provides novel pharmaceutical compositions comprising a therapeutically effective amount of the chemical compound of the invention. While a chemical compound of the invention for use in therapy may be administered in the form of the raw chemical compound, it is preferred to introduce the active ingredient, optionally in the form of a physiologically acceptable salt in a pharmaceutical composition together with one or more excipients, carriers and/or diluents.

In a preferred embodiment, the invention provides pharmaceutical compositions comprising the chemical compound of the invention or a pharmaceutically acceptable salt or derivative thereof together with one or more pharmaceutically acceptable carriers therefor and, optionally, other therapeutic and/or prophylactic ingredient. The carrier(s) must be "acceptable" in the sense of being compatible with the other ingredients of the formulation and not deleterious to the recipient thereof.

Pharmaceutical compositions those suitable for oral, rectal, nasal, topical (including buccal and sub-lingual), vaginal or parenteral (including intramuscular, subcutaneous and intravenous) administration, or in a form suitable for administration by inhalation or insufflation.

The chemical compound of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Compositions containing ten (10) milligrams of active ingredient or, more broadly, 0.1 to one hundred (100) milligrams, per tablet, are accordingly suitable representative unit dosage forms.

The chemical compound of the present invention can be administrated in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and more dispersible granules. A solid carrier can be one or more substances which may also act as diluents, flavouring agents, solubilizers, lubricants, suspending agents, binders, preservatives, tablet disintegrating agents or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "perparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

For topical administration to the epidermis the chemical compound according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in package form.

Tablets or capsules for oral administration and liquids for intravenous administration and continuous infusion are preferred compositions.

Biological Activity and Methods of Treatment

The novel indole-2,3-dione-3-oxime derivatives and the pharmaceutically acceptable salts of the invention possess valuable therapeutic properties. In particular the novel indole-2,3-dione-3-oxime derivatives of the invention are excitatory amino acid antagonists and useful in the treatment of disorders or diseases of mammals, including humans, which are responsive to excitatory amino acid receptor antagonists. The same biological activity applies to physiologic metabolites of the novel indole-2,3-dione-3-oxime derivatives of the invention.

The chemical compound of this invention is useful in the treatment of central nervous system disorders related to their biological activity. More particularly the novel indole-2,3-dione-3-oxime derivatives of the invention show strong excitatory amino acid (EAA) antagonising properties at the AMPA ((RS)-alfa-amino-3-hydroxy-5-methyl-4-isoxazolepropionic acid) binding site.

The chemical compound of this invention may accordingly be administered to a subject, including a human, in need of treatment, alleviation, or elimination of a disorder or disease associated with the biological activity of the compound. This includes especially cerebral ischaemia, cerebral infarction, excitatory amino acid dependent, including glutamate and/or aspartate dependent Lathyrism, Alzheimer's and Huntington's diseases, Amyotropic Lateral sclerosis, phychosis, Parkinsonism, epilepsy, anxiety, pain (migraine), drug addiction and convulsions.

Therefore the invention relates to the use of a chemical compound of the invention for the manufacture of a pharmaceutical composition for the treatment of a disorder or disease of a mammal, including a human, which disorder or disease is responsive to glutamic and/or aspartic acid receptor antagonists.

In a more specific aspect the invention relates to the use of a chemical compound of the invention for the manufacture of a pharmaceutical composition for the treatment a cerebrovascular disorder, lathyrism, Alzheimer's disease, Huntington's diseases, amyotrophic lateral sclerosis (ALS), schizophrenia, Parkinsonism, epilepsy, anxiety, pain or drug addiction.

Also, the invention provides a method of treating disorders or diseases of living animals, including humans, which are responsive to excitatory amino acid receptor antagonists, comprising administering to a living animal body, including a human, in need thereof an effective amount of a chemical compound of the invention.

In a more specific aspect the invention provides a method of treating a cerebrovascular disorder, lathyrism, Alzheimer's disease, Huntington's diseases, amyotrophic lateral sclerosis (ALS), schizophrenia, Parkinsonism, epilepsy, anxiety, pain or drug addiction.

Suitable dosage ranges are 0.1 to 1000 milligrams daily, 10–500 milligrams daily, and especially 30–100 milligrams daily, dependent as usual upon the exact mode of administration, form in which administered, the indication toward which the administration is directed, the subject involved and the body weight of the subject involved, and further the preference and experience of the physician or veterinarian in charge.

Methods of Preparation

The novel indole-2,3-dione-3-oxime derivatives of the invention may be prepared by conventional methods of chemical synthesis, e.g. those described in the working examples. The starting materials for the processes described in the present application are known or may readily be prepared by conventional methods from commercially available chemicals.

The end products of the reactions described herein may be isolated by conventional techniques, e.g. by extraction, crystallisation, distillation, chromatography, etc.

In yet another aspect the invention provides a method of preparing a chemical compound of the invention which comprises the step of reacting a compound having the general formula

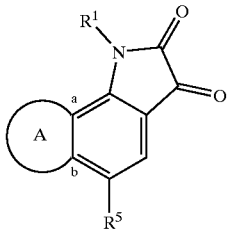

wherein $R^1$, $R^5$, and "A" have the meanings set forth above, with a compound having the formula

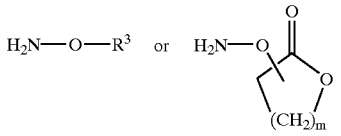

wherein $R^3$ and m have the meanings set forth above, optionally followed by converting the thus obtained compound to another compound of the invention or to a pharmaceutically acceptable salt hereof by using conventional methods.

EXAMPLES

The invention is further illustrated with reference to the following examples which are not intended to be in any way limiting to the scope of the invention as claimed.

Example 1

Preparatory Example

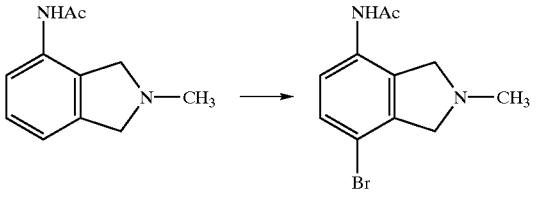

A solution of 4-acetamido-2-methyl-2H-1,3-dihydro-isoindole (10 g) and bromine (3.0 g) in trifluoroacetic acid (150 ml) was stirred at 50° C. for 40 hours. The solution was evaporated in vacuo. The residue was dissolved in water (300 ml), and pH was adjusted to neutral with sat. $Na_2CO_3$. This treatment afforded a crystalline precipitate of the product, which was collected by filtration. Yield 9g, m.p. 145°–148°.

Example 2

Preparatory Example

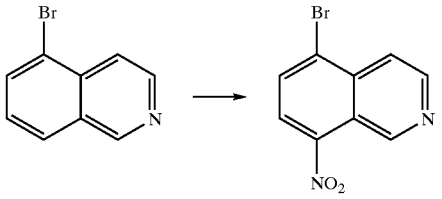

A solution of potassium nitrate (1.78 g, 8.56 mmol) was added slowly to a solution of 5-bromoisoquinoline in 12 mL $H_2SO_4$. After stirring for 3 hours the reaction mixture was poured onto ice and neutralised with conc. ammonium hydroxide. The yellow precipitate was extracted with ethyl acetate (3x), and the combined organic layers were washed with saturated NaCl, dried over $MgSO_4$, filtered and concentrated. The residue was chromatographed on silica gel (40% ethyl acetate in hexane as eluent) to give 5-bromo-3-nitroisoquinoline in 96% yield.

Example 3

Preparatory Example

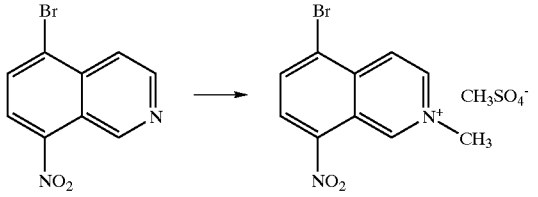

A mixture of 5-bromo-8-nitroisoquinoline (0.99 g, 3.91 mmol) and dimethylsulfate (0.41 mL) in anhydrous DMF (20 mL) was heated at 80° C. for 24 hours. After removing the DMF in vacuo, the isoquinoline methylammonium salt was obtained (used without further purification).

In a similar manner the following compound was prepared:

2-ethyl-5-bromo-8-nitroquinolinium ethylsulphate by reaction with diethyl sulphate.

Example 4

Preparatory Example

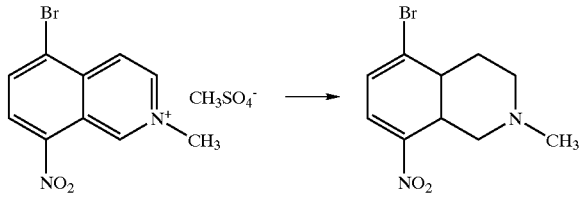

The isoquinoline salt (3.9 mmol) was dissolved in acetic acid (10 mL) and sodium borohydride (0.15 g, 3.97 mmol) was added. After stirring for 24 h, the reaction mixture was diluted with a mixture of ethyl acetate and water and potassium carbonate was added portion-wise to neutralise the acetic acid. The aqueous layer was extracted with ethyl acetate (2x), washed with saturated NaCl, dried over $MgSO_4$, filtered and evaporated. The residue was chromatographed on silica gel (30% ethyl acetate in hexane as eluent) to give the light sensitive N-methyl 5-bromo-8-nitro-1,2,3,4-tetrahydroisoquinoline (0.47 g, 45% yield).

N-ethyl-5-bromo-8-nitro-1,2,3,4-tetrahydroisoquinoline was prepared according to the same procedure. M.p. 52–53° C.

Example 5

Preparatory Example

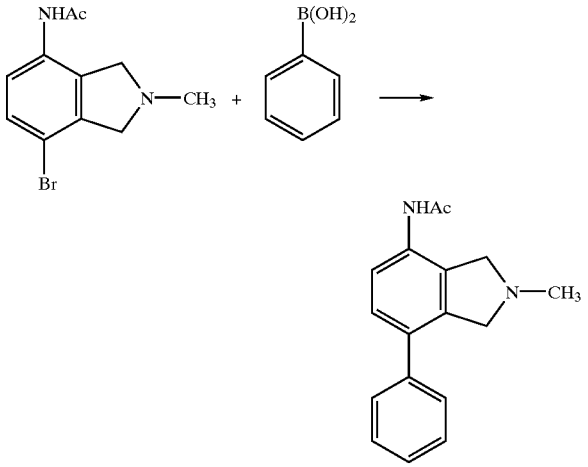

A mixture of 4-acetamido-7-bromo-2-methyl-2H-1,3-dihydro-isoindole (0.2 g), phenyl boronic acid (137 mg), tetrakis(triphenylphosphine)palladium [0] (26 mg), $NaHCO_3$, (315 mg) was stirred at reflux temperature in a mixture of water (3.75 ml) and dimethoxyethane (7.5 ml) for 90 min. After cooling to room temperature the reaction mixture was partitioned between EtOAc (25 ml) and aq. NaOH (2×5 ml, 1N). The organic phase was then dried over $Na_2SO_4$ and evaporated to give 4-acetamido-7-phenyl-2-methyl-2H-1,3-dihydro-isoindole, m.p. 160–62° C.

In a similar manner the following compounds were prepared from the appropriate bromides and boronic acids:

4-acetamido-7-phenyl-2-ethyl-2H-1,3-dihydro-isoindole, m.p. 67–68° C.;

4-acetamido-7-(1-naphthyl)-2-methyl-2H-1,3-dihydroisoindole m.p. 260–62° C.;

4-acetamido-5-nitro-7-phenyl-2-methyl-2H-1,3-dihydroisoindole m.p. 270–72° C.;

5-acetamido-2-methyl-6-nitro-8-phenyl-1,2,3,4-tetrahydro-isoquinoline m.p. 214–217° C.;

2-methyl-5-phenyl-8-nitro-1,2,3,4-tetrahydro-isoquinoline m.p. 75–78° C.(from reaction between phenyl boronic acid and 5-bromo-2-methyl-8-nitro-1,2,3,4-tetrahydro-isoquinoline);

2-methyl-5-(4-chlorophenyl)-8-nitro-1,2,3,4-tetrahydroisoquinoline m.p. 162–163° C.;

2-methyl-5-(4-trifluoromethylphenyl)-8-nitro-1,2,3,4-tetrahydro-isoquinoline m.p. 133–134° C.;

2-methyl-5-(4-fluorophenyl)-8-nitro-1,2,3,4-tetrahydro-isoquinoline m.p. 159–160° C.

5-acetamido-2-methyl-8-phenyl-1,2,3,4-tetrahydro-isoquinoline, m.p. 140–143° C.

Example 6

Preparatory Example

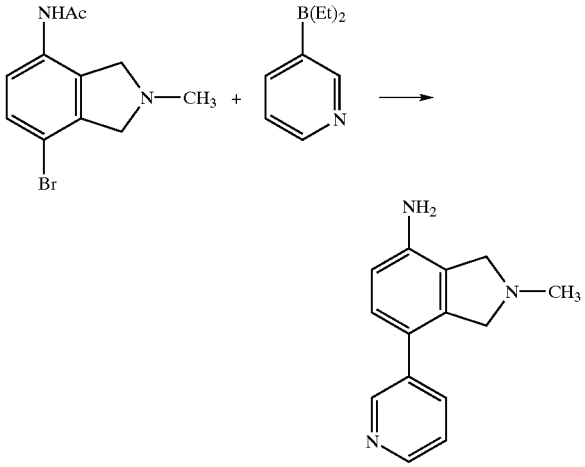

A mixture of 4-acetamido-7-bromo-2-methyl-2H-1,3-dihydro-isoindole(8 mmol), diethyl(3-pyridyl)borane, tetrakis(triphenylphosphine)palladium (0) (400 mg), powdered potassium hydroxide (32 mmol) and tetrabutylammonium bromide (4 mmol) was refluxed in THF (50 mL) for 48 hours. The mixture was then cooled to room temperature, where after EtOAc (100 mL) was added. The resulting mixture was then filtered through filter aid, and the filtrate was evaporated. The residue was partitioned between water (50 mL) and diethyl ether (25 mL). This treatment afforded a crystalline precipitate of the product which was collected by filtration and washed with water and diethylether, m.p.180–86° C.

Example 7

Preparatory Example

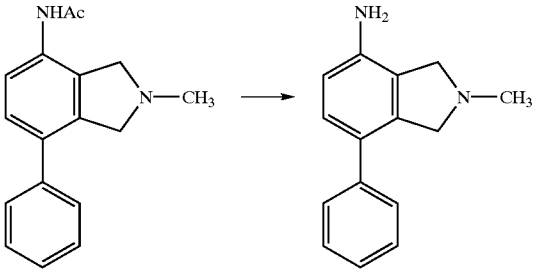

4-acetamido-7-phenyl-2-methyl-2H-1,3-dihydro-isoindole(2.6 g) was heated with stirring at 80° C., for 48 hours in sulphuric acid (66%, 25 mL), where after the solution was poured onto ice and then neutralised with aq. NaOH. The precipitated product was collected by filtration, and washed with water. M.p. 154–55° C.

Similar deacetylations gave:

4-amino-7-(1-naphthyl)-2-methyl-2H-1,3-dihydro-isoindole, m.p. 145–48° C.;

4-amino-5-nitro-7-phenyl-2-methyl-2H-1,3-dihydro-isoindole, m.p. 170–72° C.;

5-amino-2-methyl-6-nitro-8-phenyl-1,2,3,4-tetrahydro-isoquinoline, m.p. 128–130° C.;

4-amino-7-phenyl-2-ethyl-2H-1,3-dihydro-isoindole hydrochloride, m.p. 222–225° C.; and 5-amino-2-methyl-8-phenyl-1,2,3,4-tetrahydro-isoquinoline, m.p. 273–275° C.

Example 8

Preparatory Example

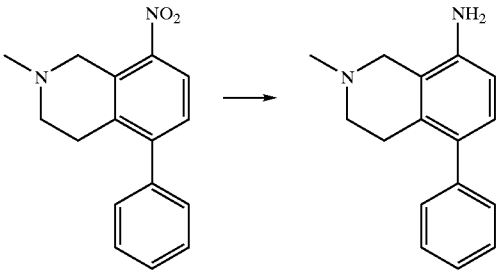

8-amino-2-methyl-5-phenyl-1,2,3,4-tetrahydro-isoquinoline hydrochloride, m.p. 210–21° C., 8-amino-2-methyl-5-(4-fluorophenyl)-1,2,3,4-tetrahydro-isoquinoline, m.p. 141° C., 8-amino-2-methyl-5-(4-trifluoromethylphenyl)-1,2,3,4-tetrahydro-isoquinoline, m.p. 132–134° C., and 8-amino-2-methyl-5-(4-chlorophenyl)-1,2,3,4-tetrahydro-isoquinoline hydrochloride, m.p. 213–215° C., were all obtained by hydrogenation using Pd/C as catalyst and ethanol as solvent.

Example 9

Preparatory Example

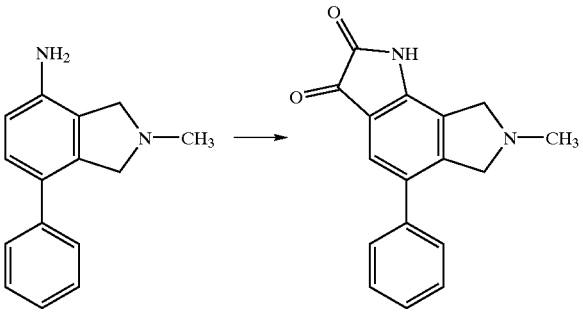

A mixture of 4-amino-7-phenyl-2-methyl-2H-1,3-dihydro-isoindole(2.0 g, 9 mmol), conc. HCl (0.83 ml), 1.5 ml chloral, 10 g of $Na_2SO_4$, $NH_2OH$ (2.0 g) in water (60 mL) was refluxed for two hours, whereafter it was cooled and neutralised with sat. $NaHCO_3$. The aqueous solution was decanted from the oily residue which was dissolved in methylene chloride (100 mL). This solution was dried over $NaSO_4$, and the solvent was removed by evaporation. The residue was dissolved in methane sulphonic acid (3 ml) and heated to 120° C. for 30 min. After cooling to ambient temperature the solution was diluted with water (20 mL) and neutralised with sat. $Na_2CO_3$. The impure product was filtered off. Pure 7-methyl-5-phenyl-1,6,7,8-tetrahydrobenzo[2,1-b:3,4-c]dipyrrole-2,3-dione m.p. 187–90° C. was obtained after column purification on silica gel using methylene chloride acetone methanol (4:1:1) as eluent.

In a similar manner the following compounds were prepared:

7-ethyl-5-phenyl-1,6,7,8-tetrahydrobenzo[2,1-b:3,4-c] dipyrrole-2,3-dione, m.p. >250° C. (decomposes);

7-methyl-5-(1-naphthyl)-1,6,7,8-tetrahydrobenzo[2,1-b:3,4-c]dipyrrole-2,3-dione-3-oxime in low yield, m.p.>300° C.;

7-methyl-5-(3-pyridyl)-1,6,7,8-tetrahydrobenzo[2,1 -b:3,4-c]dipyrrole-2,3-dione-3-oxime. NMR ($^1$H,500 MHz, 6-D DMSO):2.5 ppm (3H,S), 3.8 ppm (2H,S), 3.9ppm (2H,S), 6.5–8.7 ppm (5H aromatic, 1S, 4M), 11.0 ppm ((1H,S, NH) 13.4 ppm (1H,S,NOH);

8-methyl-5-phenyl-6,7,8,9-tetrahydro-1H-pyrrolo[3,2-h] isoquinoline-2,3-dione, m.p. 280–82° C.;

8-methyl-5-(4-chlorophenyl)-6,7,8,9-tetrahydro-1H-pyrrolo[3,2-]isoquinoline-2,3-dione, m.p. 225° C. (decomposes);

8-methyl-5-(4-trifluoromethylphenyl)-6,7,8,9-tetrahydro-1H-pyrrolo[3,2-h]isoquinoline-2,3-dione, m.p. 220–25° C.;

8-methyl-5-(4-fluorophenyl)-6,7,8,9-tetrahydro-1H-pyrrolo[3,2-h]isoquinoline-2,3-dione, m.p. 220–21° C.; and 7-methyl-5-phenyl-6,7,8,9-tetrahydro-1H-pyrrolo[2,3-f] isoquinoline-2,3-dione, m.p. >300° C.

Example 10

Preparatory example

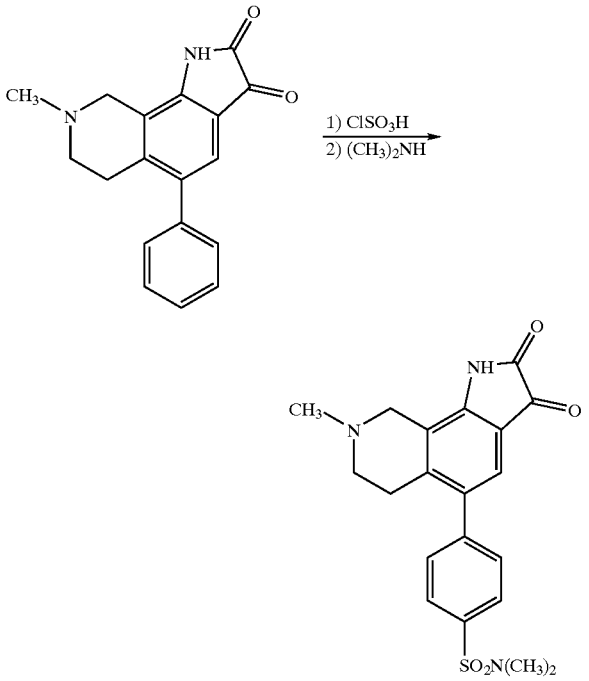

4 g of 8-methyl-5-phenyl-6,7,8,9-tetrahydro-1H-pyrrolo [3,2-h] isoquinoline-2,3-dione was added in portions to ice-cold chlorosulphonic acid (20 ml). The solution was allowed to stir at room temperature for ½ before it was cooled on ice. Excess chlorosulphonic acid was then destroyed carefully with water. After addition of 40 ml of water a heavy precipitate of the sulphonyl chloride was obtained. This solid was filtered off and washed with water whereafter, without drying, it was dissolved in tetrahydrofuran (100 ml). To this solution was drop-wise added a solution of dimethylamine in tetrahydrofuran(100 ml, 0,5M). The final mixture was stirred at room temperature for 3 hours and then evaporated. The oily residue was partitioned between water/Ethyl acetate. The organic phase was extracted with 100 ml 0,5N hydrochloric acid. The aqueous phase was separated and pH adjusted to 9. This caused a precipitate of crude product which could be purified by column cromatography.

8-methyl-5-(4-(piperidinosulfonyl)phenyl)-6,7,8,9-tetrahydro-1H-pyrrolo[3,2-h] isoquinoline-2,3-dione, m.p. >300° C. was prepared analogously.

Example 11

Preparatory Example

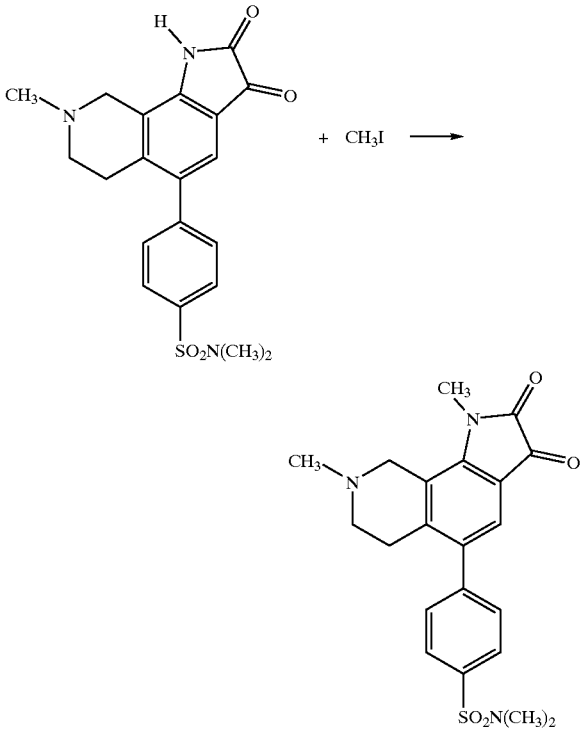

NaH 60% (110 mg, 2.8 mmol) was added at 0° C. to a mixture of 8-methyl-5-(4-(N,N-dimethylsulfamoyl)phenyl)-6,7,8,9-tetrahydro-1-H-pyrrolo[3,2-h]isoquinoline-2,3-dione (1 g, 2.5 mmol) in dimethylformamide (10 ml). The mixture was stirred at 0° C. for 10 min. Methyliodide (175 μl, 2.8 mmol) was added and the mixture was stirred or one hour at ambient temperature. The reaction mixture was poured into water (20 ml) and extracted with ethyl acetate (2×25 ml). The organic phase was dried over sodium sulphate and evaporated. Pure 1-methyl-8-methyl-5-(4-(N,N-dimethylsulfamoyl)phenyl)- 6,7,8,9-tetrahydro-pyrrolo[3,2-h]isoquinoline-2,3-dione was obtained after purification on silica gel using dichloromethane/acetone/methanol (8:1:1) as the eluent. Yield 160 mg, m.p. 232–240° C. (decomposes).

The following compound was obtained analogously:

1-methyl-8-methyl-5-phenyl-6,7,8,9-tetrahydro-pyrrolo[3,2-h]isoquinoline-2,3-dione.

Example 12

Preparatory Example

1)

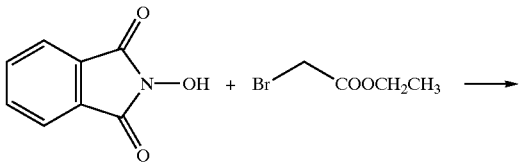

-continued

2)

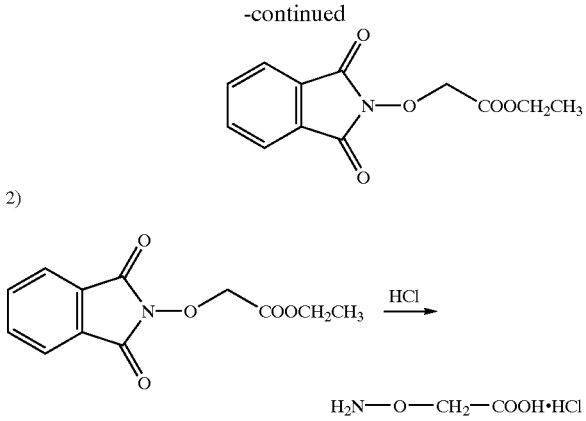

1a) To a solution of N-hydroxyphtalimide (48.9 g, 305.37 mmol) and ethyl 2-bromoacetate (51.0 ml, 459.8 mmol) in dry dimethylformamide (500 ml) was added triethylamine (84.6 ml, 610.74 mmol) and the mixture was stirred at room temperature overnight. The precipitate was filtered off and washed with dimethylformamide. The filtrate was evaporated and the residue was stirred with diluted hydrochloric acid (450 ml, 0.7M). The precipitate was filtered off and dried. Yield: 72.4 g.

1b) The compound N-(2-bromoethoxy)phtalimide was prepared analogously from 1,2-dibromoethane and N-hydroxyphtalimide.

2a) The product obtained under a) above (72.0 g 288.9 mmol) was suspended in 6M HCL (720 ml). The mixture was stirred at 100° C. for 1.5 hours. The mixture was allowed to cool to room temperature with stirring. The precipitate was filtered off and the filtrate was concentrated by evaporation. To the residue was added toluene and the mixture was evaporated to dryness. The residue thus obtained was then stirred with a mixture of toluene and ethyl acetate. This treatment resulted in precipitation of the product which was filtered off and dried. The filtrate was evaporated to dryness and the residue was triturated with methanol. This afforded a precipitate of the product which was filtered off and dried. Total yield is 25.6 g.

2b) The compound O-(2-hydroxyethyl)hydroxylamine hydrochloride was prepared analogously from the compound obtained under 1b) above.

Example 13

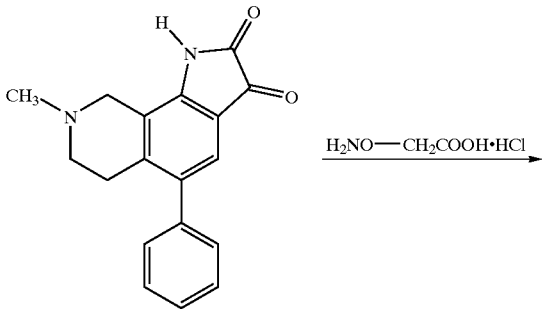

-continued

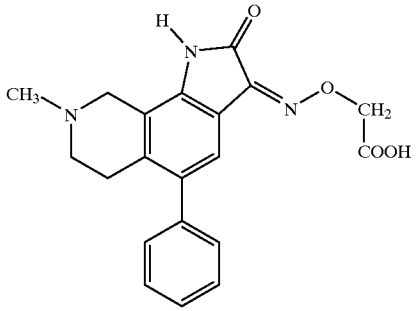

A suspension of 8-methyl-5-phenyl-6,7,8,9-tetrahydro-1H-pyrrolo[3,2-h]isoquinoline-2,3-dione (2.6 g, 8 mmol) in water (75 ml) was heated to reflux. The product of example 12 (2a) (1,1 g, 8.7 mmol) was added and heating was continued for 30 min. After cooling to room temperature, the precipitated product was filtered off.

8-methyl-5-phenyl-6,7,8,9-tetrahydro-1H-pyrrolo[3,2-h]-isoquinoline-2,3-dione-3-O-(carboxymethyl)oxime, yield 3.27 g, m.p. 283–285° C. (decomposes).

The following compounds were prepared analogously:

8-methyl-5-(4-(N,N-dimethylsulfamoyl)phenyl)-6,7,8,9-tetrahydro-1H-pyrrolo[3,2-h]-isoquinoline-2,3-dione-3-O-(carboxymethyl)oxime hydrochloride, m.p. >338° C. (decomposes);

1-methyl-8-methyl-5-phenyl-6,7,8,9-tetrahydro-pyrrolo[3,2-h]isoquinoline-2,3-dione-3-O-(carboxymethyl)oxime hydrochloride, m.p. 180–194° C. (decomposes);

1 -methyl-8-methyl-5-(4-(N,N-dimethylsulfamoyl)phenyl)-6,7,8,9-tetrahydro-pyrrolo[3,2-h]isoquinoline-2,3-dione-3-O-(carboxymethyl)oxime hydrochloride, m.p. 277–285° C. (decomposes);

8-methyl-5-(4-(N,N-dimethylsulfamoyl)phenyl)-6,7,8,9-tetrahydro-1H-pyrrolo[3,2-h]isoquinoline-2,3-dione-3-O-(2-hydroxyethyl)oxime, m.p. 163° C. (decomposes);

1-methyl-8-methyl-5-(4(N,N-dimethylsulfamoyl)phenyl)-6,7,8,9-tetrahydro-1H-pyrrolo[3,2-h]isoquinoline-2,3-dione-3-O-(1-ethoxycarbonyl-1-methylethyl)oxime methanesulfate, m.p. 250° C. (decomposes);

8-methyl-5-(4-(N,N-dimethylsulfamoyl)phenyl)-6,7,8,9-tetrahydro-1H-pyrrolo[3,2-h]isoquinoline-2,3-dione-3-O-(1-carboxy-1-methylethyl)oxime hydrochloride, m.p. 250° C. (decomposes; dark at 220° C.); and 8-methyl-5-phenyl-6,7,8,9-tetrahydro-1H-pyrrolo[3,2-h]isoquinoline-2,3-dione-3-O-(1-carboxy-1-methylethyl)oxime hydrochloride, m.p. 250° C. (decomposes; dark at 220° C.).

Example 14

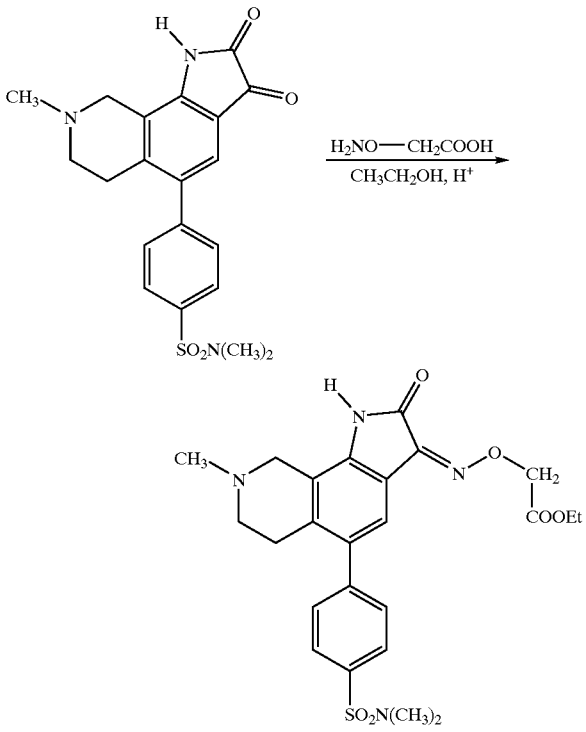

8-methyl-5-(4-(N,N-dimethylsulfamoyl)phenyl)-6,7,8,9-tetrahydro-1H-pyrrolo[3,2h]-isoquinoline-2,3-dione (3.0 g, 7.5 mmol) in dry ethanol (50 ml) was heated to reflux. The compound of example 12 (2.4 g,18.8 mmol) and HCl in ether (2–3 ml, 0.9M) was added and reflux was continued for 48 hours. Additional HCl in ether was added at intervals during the this period. The mixture was evaporated and the residue was stirred with water and neutralised with saturated $NaHCO_3$. The mixture was filtered and pure 8-methyl-5-(4-(N,N-dimethylsulfamoyl)phenyl)-6,7,8,9-tetrahydro-1H-pyrrolo[3,2h]-isoquinoline-2,3-dione-3-O-(ethoxycarbonylmethyl) oxime was obtained after purification on silica gel using dichloromethan/methanollacetone/(4:1:1) as eluent.

The compound 1-methyl-8-methyl-5-phenyl-6,7,8,9-tetrahydro-1H-pyrrolo[3,2h]-isoquinoline-2,3-dione-3-O-(ethoxycarbonylmethyl) oxime hydrochloride, m.p. 271–275° C. (decomposes) was prepared analogously.

Example 15

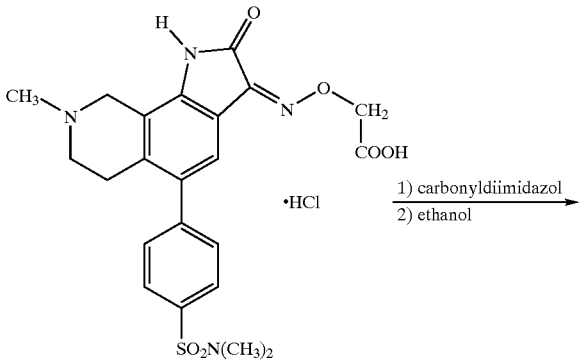

-continued

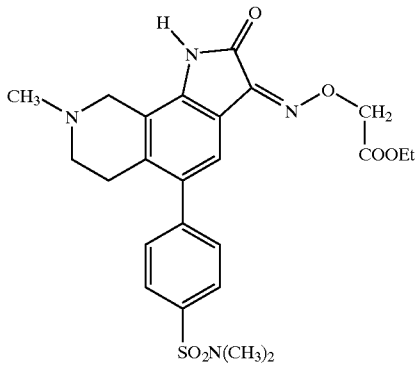

8-methyl-5-(4-(N,N-dimethylsulfamoyl)phenyl-6,7,8,9-tetrahydro-1H-pyrrolo[3,2-h]isoquinoline-2,3-dione-3-O-(carboxymethyl)oxime, HCl (1 g, 2.1 mmol) was heated to reflux in dry tetrahydrofuran (50 ml). Carbonyldiimidazol (3×4 g, 9.5 mmol) was added at 15 min intervals. Following the addition of carbonyldiimidazole, reflux was continued for 30 min. After cooling, dry ethanol (1ml, 16 mmol) was added and the mixture was stirred at room temperature overnight. The solvent was removed by evaporation. The residue was stirred with water and $NaHCO_3$. The resulting crystalline product, 8-methyl-5-(4-(N,N-dimethylsulfamoyl)phenyl-6,7,8,9-tetrahydro-1H-pyrrolo[3,2-h]isoquinoline-2,3-dione-3-O-(ethoxycarbonylmethyl) oxime was filtered off and dried. M.p. >300° C. (decomposes).

The following compounds were prepared analogously:

8-methyl-5-phenyl-6,7,8,9-tetrahydro-1H-pyrrolo[3,2-h] isoquinoline-2,3-dione-3-O-(ethoxycarbonylmethyl) oxime, m.p. 294° C. (decomposes);

8-methyl-5-phenyl-6,7,8,9-tetrahydro-1H-pyrrolo[3,2-h] isoquinoline-2,3-dione-3-O-(isopropoxycarbonylmethyl) oxime, m.p. 174–176° C. (decomposes);

8-methyl-5-phenyl-6,7,8,9-tetrahydro-1H-pyrrolo[3,2-h] isoquinoline-2,3-dione-3-O-(1-ethoxycarbonyl-1-methyl) ethyloxime, m.p. 159–169° C.;

1-methyl-8-methyl-5-(4-(N,N-dimethylsulfamoyl) phenyl-6,7,8,9-tetrahydropyrrolo[3,2-h]isoquinoline-2,3-dione-3-O-(ethoxycarbonylmethyl) oxime, m.p. 287–300° C. (decomposes);

8-methyl-5-phenyl-6,7,8,9-tetrahydro-1H-pyrrolo[3,2-h] isoquinoline-2,3-dione-3-O-(t-butoxycarbonylmethyl) oxime, m.p. 295° C. (176° C. decomposes);

8-methyl-5-phenyl-6,7,8,9-tetrahydro-1H-pyrrolo[3,2-h] isoquinoline-2,3-dione-3-O-(N,N-dimethylcarbamoylmethyl) oxime, m.p. 194–196° C.;

8-methyl-5-phenyl-6,7,8,9-tetrahydro-1H-pyrrolo[3,2-h] isoquinoline-2,3-dione-3-O-(N-methylcarbamoylmethyl) oxime, m.p. 219–221° C.;

8-methyl-5-phenyl-6,7,8,9-tetrahydro-1H-pyrrolo[3,2-h] isoquinoline-2,3-dione-3-O-(N-phenylcarbamoylmethyl) oxime, m.p. 208–210° C.;

8-methyl-5-phenyl-6,7,8,9-tetrahydro-1H-pyrrolo[3,2-h] isoquinoline-2,3-dione-3-O-(N,N-di(2-hydroxyethyl) carbamoylmethyl) oxime, m.p. 136–144° C. (decomposes);

8-methyl-5-phenyl-6,7,8,9-tetrahydro-1H-pyrrolo[3,2-h] isoquinoline-2,3-dione-3-O-(morpholinocarbonylmethyl) oxime, m.p. 216–217° C.;

8-methyl-5-phenyl-6,7,8,9-tetrahydro-1H-pyrrolo[3,2-h] isoquinoline-2,3-dione-3-O-(ethoxycarbonylmethylcarbamoylmethyl) oxime, m.p. 170–172° C.;

8-methyl-5-phenyl-6,7,8,9-tetrahydro-1H-pyrrolo[3,2-h] isoquinoline-2,3-dione-3-O-(N,N-di(2-(N,N-diethylamino) ethyl)carbamoyl) oxime, oil;

8-methyl-5-(4-(N,N-dimethylsulfamoyl)phenyl-6,7,8,9-tetrahydro-1H-pyrrolo[3,2-h]isoquinoline-2,3-dione-3-O-(cyclopropylmethoxycarbonylmethyl)oxime, m.p. 143–145° C.;

8-methyl-5-(4-(N,N-dimethylsulfamoyl)phenyl-6,7,8,9-tetrahydro-1H-pyrrolo[3,2-h]isoquinoline-2,3-dione-3-O-(isopropoxycarbonylmethyl)oxime, m.p. >300° C.;

8-methyl-5-(4-(N,N-dimethylsulfamoyl)phenyl-6,7,8,9-tetrahydro-1H-pyrrolo[3,2-h]isoquinoline-2,3-dione-3-O-(N,N-dimethyl-carbamoylmethyl)oxime, m.p. 183–185° C.;

8-methyl-5-(4-(N,N-dimethylsulfamoyl)phenyl-6,7,8,9-tetrahydro-1H-pyrrolo[3,2-h]isoquinoline-2,3-dione-3-O-(piperdinocarbonylmethyl)oxime methane sulphate, m.p. 200–211° C. (decomposes);

8-methyl-5-(4-(piperidinosulfonyl)phenyl-6,7,8,9-tetrahydro-1H-pyrrolo[3,2-h]isoquinoline-2,3-dione-3-O-(piperidinocarbonylmethyl)oxime methane sulphate, m.p. 195–215° C. (decomposes); and 8-methyl-5-(4-(N,N-dimethylsulfamoyl)phenyl-6,7,8,9-tetrahydro-1H-pyrrolo[3,2-h]isoquinoline-2,3-dione-3-O-(morpholinocarbonylmethyl)oxime, m.p. 222–224° C.

Example 16

Preparatory Example

3-Methoxy-5-methylisoxazole

To a solution of 3-hydroxy-5-methylisoxazole (13.5 g, 136 mmol) in ether (100 mL) was added diazomethane until a persistent yellow colour was obtained. The reaction was stirred for another 30 min at room temperature. The ether was evaporated off and the residue purified by column chromatography on silica gel using ether as eluent. 9 g of the desired material was obtained.

Example 17

Preparatory Example

3-Hydroxy-4,5-dimethylisoxazole

To a solution of hydroxylamine hydrochloride (12.1 g, 0.17 mol) in methanol/water(1:5, 60 mL) was added sodium hydroxide (7.7 g, 0.19 mol) in 20 mL water. The reaction was cooled to −70° C. and filtered. The cold (−70° C.) filtrate was added to a cold (−70° C.) solution of ethyl-2-methylacetoacetate (12.5 g, 87 mmol) and sodium hydroxide (3.6 g, 90 mmol) in methanol/water (1:5, 60 mL). The reaction was stirred at −70° C. for another 2 hr. Acetone (13 mL) was added and the reaction poured into 10% aqueous hydrochloric acid heated to 80° C. The final mixture was kept at 75–80° C. for another 30 min. Extraction with ether (6×150 mL), drying of the combined extracts over magnesium sulphate and subsequent filtration and evaporation of the solvent afforded 8.1 g of the desired material.

The following compounds was prepared analogously:

3-hydroxy-4-methyl-5-tertbutylisoxazole.

Example 18

Preparatory Example

N,4,5-trimethyl-3-isoxazolone

To a solution of 3-hydroxy-4,5-dimethylisoxazole (7 g, 62 mmol) in ether (50 mL) was added diazomethane until a persistent yellow colour was obtained. The reaction was stirred for another 30 min at room temperature. The ether was evaporated off and the residue purified by column chromatography on silica gel suing either as eluent. 4 g of the desired material was obtained.

The following compounds were prepared analogously:
N,4-dimethyl-5-tertbutyl-3-isoxazolone; and
3-methoxy-4,5-dimethylisoxazolone.

Example 19

Preparatory Example

3-Methoxy-4-bromo-5-bromomethyl-isoxazole

To a solution of 3-methoxy-5-methylisoxazole (9 g, 79,6 mmol), heated to reflux, in tetrachloromethane (120 mL) was added N-bromosuccinimide (17,7 g, 99.5 mmol) in four portions over 2 hours. Catalytic amounts of benzoylperoxide was added at the same time as the first and the third portion of N-bromosuccinimide. The reaction was cooled to 10° C. and filtered. The filtrate was evaporated to dryness and the residue purified by column chromatography on silica gel using petroleum ether/ether (3:2) as eluent. 10 g of the desired material was obtained.

The following compounds were prepared analogously:
4-bromomethyl-N,5-dimethyl-3-isoxazolone;
4-bromomethyl-N-methyl-5-tertbutyl-3-isoxazolone; and
4-bromomethyl-3-methoxy-5-methylisoxazole.

Example 20

Preparatory Example

α-Phthalimidooxy-y-butyrolactone, hydrochloride

To a solution of α-Bromo-y-butyrolactone (3.0 mL, 36 mmol) in dimethylformamide (50 mL) was added N-hydroxyphthalimide (4.6 g, 28 mmol) followed by triethylamine (7.7 mL, 56 mmol). After stirring for 4 hours at room temperature the reaction was filtered and evaporated to dryness using an oil pump. Hydrochloric acid (1M, 28 mL) and water (20) mL) was added. The precipitate was filtered off and washed with water. Drying in the air gave 7.1 g of beige crystals.

The following compounds were prepared analogously:
4-bromo-3-methoxy-5-phthalimidooxymethylisoxazole;
N,5-dimethyl-4-phthalimidooxy methyl-3-isoxazolone;
N-methyl-4-phthalim idooxymethyl-5-tertbutyl-3-isoxazol one: and
4-phthalimidooxymethyl-3-methoxy-5 -methylisoxazole.

Example 21

Preparatory Example

α-Aminooxy-γ-butyrolactone hydrochloride

α-Phthalimidooxy-γ-butyrolactone (1.0 g, 4 mmol) was added to hydrochloric acid (1M, 10 mL) at reflux. After 5 min. at reflux for 5 min and the reaction was cooled down on an ice bath and filtered. The filtrate was evaporated to dryness. Toluene was added and residual water removed axeotropic distillation. 0.75 g of the desired material was obtained.

The following compounds were prepared analogously:
4-bromo-3-methoxy-5-aminooxymethylisoxazole hydrochloride;
N,5-dimethyl-4-aminooxymethyl-3-isoxazolone hydrochloride;
N-methyl-4-aminooxymethyl-5-tertbutyl-3-isoxazolone hydrochloride; and
4-aminooxymethyl-3-methoxy-5-methylisoxazole hydrochloride.

Example 22

To a solution of 8-methyl-5-(4-(N,N-dimethylsulfamoyl) phenyl)-6-7-8-9-tetrahydro-1H-pyrrolo[3,2-h]isoquinoline-2,3-dione (1.06 g, 2.7 mmol) in methanol (30 mL) heated to reflux, was added α-aminooxy-γ-butyrolactone (0.75 g, 4 mmol) dissolved in warm methanol (10 mL). Yellow crystals precipitate out. The reaction was heated at reflux for another 15 min and cooled to room temperature. The product was filtered off and washed with cold methanol.

0.88 g of 8-methyl-5-(4-(N,N-dimethylsulfamoyl) phenyl)-6-7-8-9-tetrahydro-1H-pyrrolo[3,2-h]-isoquinoline-2,3-dione-3-O-(3-(2-oxo)tetrahydrofuryl) oxime, hydrochloride was obtained. M.p. 245° C. (decomposes).

The following compounds were prepared analogously:

8-methyl-5-(4-(N,N-dimethylsulfamoyl)phenyl)6-7-8-9-tetrahydro-1H-pyrrolo[3,2h]-isoquinoline-2,3-dione-3-O-(5-(4-bromo-3-ethoxy)isoxazolylmethyl)oxime hydrochloride. M.p. 265° C. (decomposes);

8-methyl-5-(4-(N,N-dimethylsulfamoyl)phenyl)-6-7-8-9-tetrahydro-1H-pyrrolo[3,2h]-isoquinoline-2,3-dione-3-O-(4-(5-dimethyl-3-xo)isoxazolylmethyl)oxime hydrochloride. M.p. 260° C. (decomposes);

8-methyl-5-(4-(N,N-dimethylsulfamoyl)phenyl)-6-7-8-9-tetrahydro-1H-pyrrolo[3,2h]-isoquinoline-2,3-dione-3-O-(4-(N-methyl-5-tertbutyl-3-oxo)isoxazolylmethyl)oxime hydrochloride. M.p. 260° C. (decomposes); and 8-methyl-5-(4-(N,N-dimethylsulfamoyl)phenyl)-6-7-8-9-tetrahydro-1H-pyrrolo[3,2h]-isoquinoline-2,3-dione-3-O-(4-(5-methyl-3-ethoxy(isoxazolylmethyl)oxime hydrochloride.

Example 23

8-methyl-5-(4-(N,N-dimethylsulfamoyl)phenyl)-6-7-8-9-tetrahydro-1H-pyrrolo[3,2-h]-isoquinoline-2,3-dione-3-O-(3-(2-oxo) tetrahydrofuryl)oxime (0.6 g) was stirred at room temperature for 24 hours in water (5 ml) and 1N NaOH (aq) in such amounts that assured a pH around 12. The reaction mixture was extracted with ethylacetate. The aqueous layer was separated and reduced in vacuo to a volume of 2 ml. Addition of isopropanol (10–15 ml) afforded a yellow solid precipitate of the title compound.

8-methyl-5-(4-(N,N-dimethylsulfamoyl)phenyl)-6-7-8-9-tetrahydro-1H-pyrrolo[3,2-h]-isoquinoline-2,3-dione-3-O-(4-hydroxybutyric acid-2-yl)oxime sodium salt, m.p. >200° C. (decomposes; dark at 190° C.).

Example 24

Biological Activity

In an in vitro activity (receptor affinity) test, the chemical compounds of the present invention have been tested for their affinity for the AMPA receptor.

L-glutamate (GLU) is the major excitatory neurotransmitter in the mammalian central nervous system. From electro-physiological- and binding studies, there appear to be at least three subtypes of GLU receptors, tentatively named N-methyl-D-aspartate (NMDA) receptors, quisqualate receptors and kainate receptors. AMPA has been known for several years to be a potent and selective agonist at the traditionally named quisqualate receptors. Activation of quisqualate receptors by AMPA is associated with $Na^+$influx and $K^+$efflux leading to depolarisation. $^3$H-AMPA is a selective radioligand for labelling the ionotropic quisqualate (AMPA) receptors.

Tissue preparation

Preparations are performed at 0–4° C. unless otherwise indicated. Cerebral cortex from male Wistar rats (150–200 g) is homogenised for 5–10 sec in 20 ml Tris-HCl (30 mM, pH 7.4) using an Ultra-Turrax™ homogeniser. The suspension is centrifuged at 27,000×g for 15 minutes and the pellet is washed three times with buffer (centrifuged at 27,000×g for 10 minutes). The washed pellet is homogenised in 20 ml of buffer and incubated on a water bath (of 37° C.) for 30 minutes to remove endogenous glutamate and then centrifuged for 10 minutes at 27,000×g. The pellet is then homogenised in buffer and centrifuged at for 10 minutes at 27,000×g. The final pellet is resuspended in 30 ml buffer and the preparation is frozen and stored at −20° C.

Assay

The membrane preparation is thawed and centrifuged at 2° C. for 10 minutes at 27,000×g. The pellet is washed twice with 20 ml 30 mM Tris-HCl containing 2.5 mM $CaCl_2$, pH 7.4, using an Ultra-Turrax™ homogeniser and centrifuged for 10 minutes at 27,000×g. The final pellet is resuspended in 30 mM Tris-HCl containing 2.5 mM $CaCl_2$ and 100 mM KSCN, pH 7.4 (100 ml per g of original tissue) and used for binding assays. Aliquots of 0.5 (0.2) ml are added to 25 (20) μl of test solution and 25 (20) μl of $^3$H-AMPA (5 nM, final concentration), mixed and incubated for 30 minutes at 2° C. Non-specific binding is determined using L-glutamate (0.6 mM, final concentration).

After incubation the 550 μl samples are added 5 ml of ice-cold buffer and poured directly onto Whatman™ GF/C glass fibre filters under suction and immediately washed with 5 ml of ice-cold buffer. The 240 μl samples are filtered over glass fibre filter using a Skatron™ cell harvester. The filters are washed with 3 ml ice-cold buffer. The amount of radioactivity on the filters is determined by conventional liquid scintillation counting. Specific binding is total binding minus non-specific binding.

The test value is given as the $IC_{50}$ (the concentration (μM) of the test substance which inhibits the specific binding of $^3$H-AMPA by 50%).

From this test it was found that:

8-methyl-5-(4-(N,N-dimethylsulphamoyl)phenyl-6,7,8,9-tetrahydro-1H-pyrrolo[3,2-h]isoquinoline-2,3-dione-3-O-(ethoxycarbonylmethyl)oxime of the invention have an $IC_{50}$ value of 0.1 μM;

8-methyl-5-(4-(N,N-dimethylsulfamoyl)phenyl)-6-7-8-9-tetrahydro-1H-pyrrolo[3,2-h]-isoquinoline-2,3-dione-3-O-(3-(2-oxo)tetrahydrofuryl)oxime of the invention have an $IC_{50}$ value of 0.15 μM; and 8-methyl-5-(4-(N,N-dimethylsulfamoyl)phenyl)-6-7-8-9-tetrahydro-1H-pyrrolo[3,2-h]-isoquinoline-2,3-dione-3-O-(4-hydroxybutyric acid-2-yl)oxime of the invention have an $IC_{50}$ value of 0.05 μM.

What is claimed is:

1. A compound represented by the formula (I):

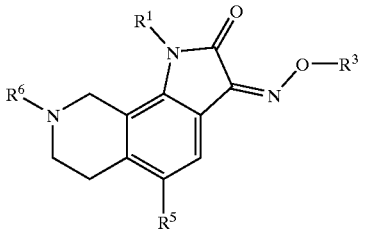

wherein $R^1$ represents hydrogen or lower alkyl;

$R^3$ represents *a lactone ring of the formula* (*VI*):

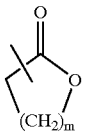

*wherein m is 2, or*

$R^3$ *represents* a group of the formula

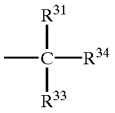

wherein $R^{31}$ and $R^{33}$ independently of each other represent hydrogen[or], lower alkyl, *or hydroxyalkyl;* and $R^{34}$ represents carboxy, alkoxycarbonyl, cycloalkylalkoxycarbonyl, a group of the formula —$CONR^{35}R^{36}$, or Het; wherein $R^{35}$ and $R^{36}$ represent hydrogen, lower alkyl, hydroxyalkyl, phenyl, or a group of the formula —$CH_2$—$R^{37}$, wherein $R^{37}$ represents carboxy or alkoxycarbonyl; or $R^{35}$ and $R^{36}$ together with the N-atom to which they are attached form a saturated 6-membered heterocyclic ring, optionally containing one additional O atom; and Het represents a saturated or unsaturated 5-membered monocyclic, heterocyclic ring, containing N and/or O as the heteroatom, which ring may optionally be substituted one or more times with substituents selected from the group consisting of halogen, lower alkyl, *lower alkoxy,* and oxo;

$R^5$ represents a phenyl group, which may be substituted once with a group of the formula —$SO_2NR^{51}R^{52}$; wherein $R^{51}$ and $R^{52}$ each independently represents hydrogen or lower alkyl; or $R^{51}$ and $R^{52}$ together with the N-atom to which they are attached form a saturated 6-membered monocyclic, heterocyclic ring; and $R^6$ represents hydrogen or lower alkyl;

or a pharmaceutically acceptable salt thereof.

2. The compound according to claim 1, wherein $R^3$ represents a lacton ring of the formula (VI):

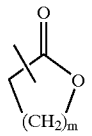

wherein m is 2.

3. The compound according to claim 1, wherein $R^3$ represents a lactone of the formula (VII):

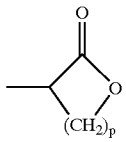

wherein p is 2.

4. A compound according to claim 1, which is 8-methyl-5-(4-(N,N-dimethylsulfamoyl)phenyl)-6-7-8-9-tetrahydro-1H-pyrrolo[3,2-h]-isoquinoline-2,3-dione-3-O-(3-(2-oxo)tetrahydrofuryl)oxime;

8-methyl-5-(4-(N,N-dimethylsulfamoyl)phenyl)-6-7-8-9-tetrahydro-1H-pyrrolo[3,2-h]-isoquinoline-2,3,dione-3-O-(5-(5-(4-bromo-3-methoxy)isoxazolylmethyl) oxime;

8-methyl-5-(4-(N,N-dimethylsulfamoyl)phenyl)-6-7-8-9-tetrahydro-1H-pyrrolo[3,2-h]-isoquinoline-2,3-dione-3-O-(5-(4-bromo-3-ethoxy)isoxazolylmethyl)oxime;

8-methyl-5-(4-(N,N-dimethylsulfamoyl)phenyl)-6-7-8-9-tetrahydro-1H-pyrrolo[3,2-h]-isoquinoline-2,3-dione-3-O-(4-(N,5-dimethyl-3-oxo)isoxazolylmethyl)oxime;

8-methyl-5-(4-(N,N-dimethylsulfamoyl)phenyl)-6-7-8-9-tetrahydro-1H-pyrrolo[3,2-h]-isoquinoline-2,3-dione-3-O-(4-(N-methyl-5-tertbutyl-3-oxo)isoxazolylmethyl)oxime;

8-methyl-5-(4-(N,N-dimethylsulfamoyl)phenyl)-6-7-8-9-tetrahydro-1H-pyrrolo[3,2-h]-isoquinoline-2,3-dione-3-O-(4-(5-methyl-3-methoxy)isoxazolylmethyl)oxime;

8-methyl-5-(4-(N,N-dimethylsulfamoyl)phenyl)-6-7-8-9-tetrahydro-1H-pyrrolo[3,2-h]-isoquinoline-2,3-dione-3-O-(4-(5-methyl-3-ethoxy)isoxazolylmethyl)oxime;

1-methyl-8-methyl-5-phenyl-6,7,8,9-tetrahydro-pyrrolo[3,2-h]isoquinoline-2,3-dione-3-O-(carboxymethyl)oxime;

1-methyl-8-methyl-5-phenyl-6,7,8,9-tetrahydro-1H-pyrrolo[3,2-h]-isoquinoline-2,3-dione-3-O-(ethoxycarbonylmethyl)oxime;

1-methyl-8-methyl-5-(4-(N,N-dimethylsulfamoyl)phenyl)-6,7,8,9-tetrahydro-pyrrolo[3,2-h]isoquinoline-2,3-dione-3-O-(carboxymethyl)oxime;

1-methyl-8-methyl-5-(4-(N,N-dimethylsulfamoyl)phenyl)-6,7,8,9-tetrahydro-1H-pyrrolo[3,2-h]isoquinoline-2,3-dione-3-O-(1-ethoxycarbonyl-1-methylethyl)oxime;

1-methyl-8-methyl-5-(4-(N,N-dimethylsulfamoyl)phenyl-6,7,8,9-tetrahydro-pyrrolo[3,2-h]isoquinoline-2,3-dione-3-O-(ethoxycarbonylmethyl)oxime;

8-methyl-5-phenyl-6,7,8,9-tetrahydro-1H-pyrrolo[3,2-h]-isoquinoline-2,3-dione-3-O-(carboxymethyl)oxime;

8-methyl-5-phenyl-6,7,8,9-tetrahydro-1H-pyrrolo[3,2-h]isoquinoline-2,3-dione-3-O-(1-carboxy-1-methylethyl)oxime;

8-methyl-5-phenyl-6,7,8,9-tetrahydro-1H-pyrrolo [3,2-h]isoquinoline-2,3-dione-3-O-(ethoxycarbonylmethyl)oxime;

8-methyl-5-phenyl-6,7,8,9-tetrahydro-1H-pyrrolo [3,2-h]isoquinoline-2,3-dione-3-O-(isopropoxycarbonylmethyl)oxime;

8-methyl-5-phenyl-6,7,8,9-tetrahydro-1H-pyrrolo [3,2-h]isoquinoline-2,3-dione-3-O-(1-ethoxycarbonyl-1-methyl)ethyloxime;

8-methyl-5-phenyl-6,7,8,9-tetrahydro-1H-pyrrolo [3,2-h]isoquinoline-2,3-dione-3-O-(t,butoxycarbonylmethyl)oxime;

8-methyl-5-phenyl-6,7,8,9-tetrahydro-1H-pyrrolo [3,2-h]isoquinoline-2,3-dione-3-O-(N,N-dimethylcarbamoylmethyl)oxime;

8-methyl-5-phenyl-6,7,8,9-tetrahydro-1H-pyrrolo [3,2-h]isoquinoline-2,3-dione-3-O-(N-methylcarbamoylmethyl)oxime;

8-methyl-5-phenyl-6,7,8,9-tetrahydro-1H-pyrrolo [3,2-h]isoquinoline-2,3-dione-3-O-(N-phenylcarbamoylmethyl)oxime;

8-methyl-5-phenyl-6,7,8,9-tetrahydro-1H-pyrrolo [3,2-h]isoquinoline-2,3-dione-3-O-(N,N-di(2-hydroxyethyl)carbamoylmethyl)oxime;

8-methyl-5-phenyl-6,7,8,9-tetrahydro-1H-pyrrolo [3,2-h]isoquinoline-2,3-dione-3-O-(morpholinocarbonylmethyl)oxime;

8-methyl-5-phenyl-6,7,8,9-tetrahydro-1H-pyrrolo [3,2-h]isoquinoline-2,3-dione-3-O-(ethoxycarbonylmethylcarbamoylmethyl)oxime;

[8-methyl-5-phenyl-6,7,8,9-tetrahydro-1H-pyrrolo [3,2-h]isoquinoline-2,3-dione-3-O-(N,N-di(2-(N,N-diethylamino)ethyl)carbamoyl)oxime;]

8-methyl-5-(4-(N,N-dimethylsulfamoyl)phenyl)-6,7,8,9-tetrahydro-1H-pyrrolo[3,2-h]-isoquinoline-2,3-dione-3-O-(carboxymethyl)oxime;

[8-methyl-5-(4-(N,N-dimethylsulfamoyl)phenyl)-6,7,8,9-tetrahydro-1H-pyrrolo[3,2-h]isoquinoline-2,3-dione-3-O-(2-hydroxyethyl)oxime;]

8-methyl-5-(4-(N,N-dimethylsulfamoyl)phenyl)-6,7,8,9-tetrahydro-1H-pyrrolo[3,2-h]isoquinoline-2,3-dione-3-O-(1-carboxy-1-methylethyl)oxime;

8-methyl-5-(4-(N,N-dimethylsulfamoyl)phenyl)-6,7,8,9-tetrahydro-1H-pyrrolo[3,2-h]isoquinoline-2,3-dione-3-O-(ethoxycarbonylmethyl)oxime;

8-methyl-5-(4-(N,N-dimethylsulfamoyl)phenyl-6,7,8,9-tetrahydro-1H-pyrrolo[3,2-h]isoquinoline-2,3-dione-3-O-(cyclopropylmethoxycarbonylmethyl)oxime;

8-methyl-5-(4-(N,N-dimethylsulfamoyl)phenyl-6,7,8,9-tetrahydro-1H-pyrrolo[3,2-h]isoquinoline-2,3-dione-3-O-(isopropoxycarbonylmethyl)oxime;

8-methyl-5-(4-(N,N-dimethylsulfamoyl)phenyl-6,7,8,9-tetrahydro-1H-pyrrolo[3,2-h]isoquinoline-2,3-dione-3-O-(N,N-dimethylcarbamoylmethyl)oxime;

8-methyl-5-(4-(N,N-dimethylsulfamoyl)phenyl-6,7,8,9-tetrahydro-1H-pyrrolo[3,2-h]isoquinoline-2,3-dione-3-O-(piperidinocarbonylmethyl)oxime;

8-methyl-5-(4-(piperdinosulfonyl)phenyl-6,7,8,9-tetrahydro-1H-pyrrolo[3,2-h]isoquinoline-2,3-dione-3-O-(piperidinocarbonylmethyl)oxime;

8-methyl-5-(4-(N,N-dimethylsulfamoyl)phenyl-6,7,8,9-tetrahydro-1H-pyrrolo[3,2-h]isoquinoline-2,3-dione-3-O-(morpholinocarbonylmethyl)oxime; or 8-methyl-5-(4-(N,N-dimethylsulfamoyl)phenyl-6,7,8,9-tetrahydro-1H-pyrrolo[3,2-h]isoquinoline-2,3-dione-3-O-(4-hydroxybutyric acid-2-yl)oxime;

or a pharmaceutically acceptable salt [hereof] *thereof*.

5. A pharmaceutical composition comprising a therapeutically effective amount of the compound according to any one of claims 1–4 together with a pharmaceutically acceptable excipient, carrier or diluent.

6. A method of preparing a compound according to any of claims 1–4 which method comprises the step of reacting a compound having the formula:

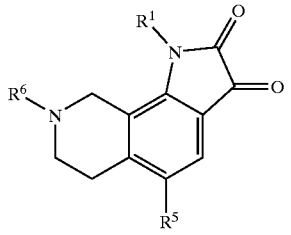

wherein $R^1$, $R^5$, and $R^6$ have the meanings set forth in claim 1 with a compound having the formula
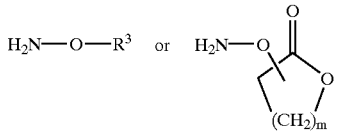
wherein $R^3$ and m have the meanings set forth in claim 1, optionally followed by converting the thus obtained compound to another compound of any of claims 1–4 or to a pharmaceutically acceptable salt thereof.
* * * * *